United States Patent

Itaya et al.

[11] 4,176,189
[45] Nov. 27, 1979

[54] INSECTICIDAL AND ACARICIDAL HYDANTOIN N-METHYLOL ESTERS

[75] Inventors: Nobushige Itaya, Nishinomiya; Masachika Hirano, Ibaraki, both of Japan

[73] Assignee: Sumitomo Chemical Company, Limited, Osaka, Japan

[21] Appl. No.: 909,107

[22] Filed: May 24, 1978

[30] Foreign Application Priority Data

Jun. 20, 1977 [JP] Japan .................................. 52-73721

[51] Int. Cl.$^2$ ................. A61K 31/415; C07D 233/72; C07D 405/12
[52] U.S. Cl. .............................. 424/273 R; 548/309; 548/312; 542/429
[58] Field of Search ............................ 548/312, 309; 424/273 R; 542/429

[56] References Cited

U.S. PATENT DOCUMENTS

| | | | |
|---|---|---|---|
| 3,213,104 | 10/1965 | Cashin et al. | 548/312 |
| 3,676,454 | 7/1972 | Vida | 548/312 |
| 3,681,377 | 8/1972 | Singhal | 548/309 |
| 3,702,333 | 11/1972 | Nakanishi et al. | 260/345.9 |
| 3,857,858 | 12/1974 | Itaya et al. | 260/332.2 R |
| 3,857,863 | 12/1974 | Ohno et al. | 260/332.2 R |
| 3,862,174 | 1/1975 | Mizutani et al. | 260/332.2 R |
| 4,053,620 | 10/1977 | Enders | 548/309 |

OTHER PUBLICATIONS

Kato et al., Agr. Biol. Chem. 1964, vol. 28, pp. 914–915.
Elliott et al., Nature 1967, pp. 493–494.
Noller, Chemistry of Organic Compounds, Saunders, Phila., 1958, 2nd Ed., p. 156.

*Primary Examiner*—John M. Ford
*Assistant Examiner*—Natalia Harkaway

*Attorney, Agent, or Firm*—Stevens, Davis, Miller & Mosher

[57] ABSTRACT

Hydantoin N-methylol esters of the formula,

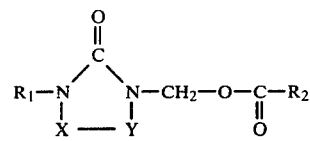

wherein one of X and Y is a carbonyl group and the other is a methylene, ethylidene or propylidene group, $R_1$ is a lower alkyl, lower alkenyl or lower alkynyl having up to 3 carbon atoms, $R_2$ is a group represented by the formula,

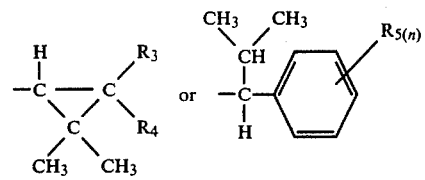

in which $R_3$ is a hydrogen atom or a methyl group; when $R_3$ is a hydrogen atom, $R_4$ is a methoxyiminomethyl or 2,2-disubstituted vinyl group in which the substituents can be selected from the group consisting of methyl, vinyl, fluorine, chlorine and bromine, or both of the substituents may form tetramethylene chain; when $R_3$ is a methyl group, $R_4$ is a methyl group; $R_5$ is a methyl, methoxy, fluorine, chlorine, bromine or 3,4-methylenedioxy group; and n is 1 or 2, a process for producing the same, insecticides and acaricides containing the same as an active ingredient, and novel intermediate compounds.

29 Claims, No Drawings

INSECTICIDAL AND ACARICIDAL HYDANTOIN N-METHYLOL ESTERS

The present invention relates to novel carboxylic acid esters of the formula (I),

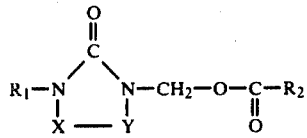

wherein one of X and Y is a carbonyl group, and the other is a methylene, ethylidene or propylidene group, $R_1$ is a lower alkyl, lower alkenyl or lower alkynyl having up to 3 carbon atoms, $R_2$ is a group represented by the formula,

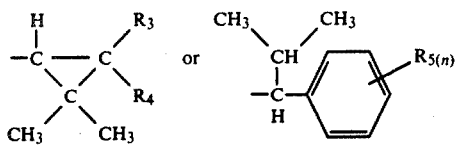

in which $R_3$ is a hydrogen atom or a methyl group; when $R_3$ is a hydrogen atom, $R_4$ is a methoxyiminomethyl or 2,2-disubstituted vinyl group in which substituents can be selected from the group consisting of methyl, vinyl, fluorine, chlorine and bromine, or both of the substituents may form tetramethylene chain; when $R_3$ is a methyl group, $R_4$ is a methyl group; $R_5$ is a methyl, methoxy, fluorine, chlorine, bromine or 3,4-methylenedioxy group; and n is 1 or 2, a process for producing the same, and insecticides and acaricides containing the same as an active ingredient.

Hitherto, various kinds of cyclopropanecarboxylic acid ester series insecticide are well known and some of them are present in pyrethrum extracts.

Among many insecticides now in practical use, these pyrethrum extracts have been widely used for controlling harmful insanitary insects and insects harmful to agricultural crops and household horticultural plants since they are very superior as insecticides in the following points: They have a strong insecticidal activity, low toxicity to mammals and rapid effect against harmful insects, and moreover harmful insects cannot easily acquire a resistance to the pesticides. On the other hand, they have also drawbacks, for example, they are high in cost so that their application range is limited from the economical point of view. Accordingly, many homologues have been synthesized by many investigators, but there are very few which are superior to natural pyrethrin or allethrin in terms of wide applicability and relation between effect and cost.

What is most important in harmful insect controlling agents is that they can rapidly knock down and kill harmful insects thereby preventing the harm by the insects.

The inventors extensively searched for insecticides having the aforesaid desirable characteristics, and found that novel carboxylic acid esters of the formula (I) were superior in the knockdown effect and insecticidal and-/or acaricidal activity on harmful insanitary insects or acarids and moreover were easily synthesized.

Synthesis of this ester will be explained hereinafter.

The ester of the formula (I) is obtained by reacting an alcohol or its halide of the formula (II),

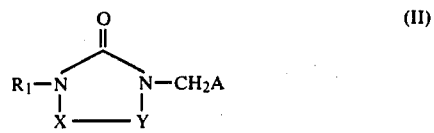

wherein $R_1$, X and Y are as defined above and A is a hydroxyl group or a halogen atom such as chlorine or bromine, with approximately equimolar amounts of a carboxylic acid of the formula (III) or (IV),

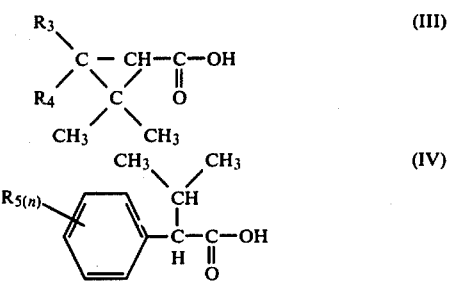

wherein $R_3$, $R_4$, $R_5$ and n are as defined above, or reactive derivative thereof optionally in the presence of a suitable reaction assistant. The reactive derivative referred to herein means acid halides, (mixed) acid anhydrides, alkali metal salts and organic tertiary base salts. When an alcohol of the formula (II), (i.e. A represents hydroxyl in this case) and a carboxylic acid of the formula (III) or (IV) are used, the reaction is generally conducted under conditions which promote dehydration. That is, the alcohol is reacted with the carboxylic acid in the presence of more than 1 mole of dehydrating agent such as dicyclohexylcarbodiimide in a suitable solvent such as benzene, toluene, diethyl ether or the like, at a temperature between about 10° C. and the boiling point of the solvent used, and the reaction is continued for the period of 30 minutes to about 1 day. When the alcohol of the formula (II) (i.e. A represents hydroxyl in this case) and an acid halide, preferably the chloride or the bromide, of the formula (III) or (IV) are used, the reaction is conducted in a suitable solvent such as benzene, toluene, diethyl ether or the like, at a temperature between about 0° C. and the boiling point of the solvent used, and in the presence of more than 1 mole of an acid acceptor, for example, an organic tertiary amine, e.g. pyridine or triethylamine. The reaction is accomplished soon after mixing the reactants.

When a (mixed) acid anhydride is used in place of the acid halide, the reaction is conducted in the same manner, except that the reaction is achieved more slowly and is favorably conducted at an elevated temperature.

When a halide of the formula (II) (i.e. A represents chlorine or bromine in this case) is used, the carboxylic acid of the formula (III) or (IV), is used in the form of an alkali metal salt or organic tertiary base salt, or may be added to the reaction system as they are together with the corresponding base.

In this process, it is desirable to use a solvent such as benzene or acetone and to heat the reaction system at the boiling point or below of the solvent.

The alcohol of the formula (II) (i.e. A is hydroxyl) is readily obtained by reaction of the appropriate hydantoin of the formula (V) with formaldehyde or its equivalences (e.g. paraformaldehyde) (an analogous reaction is shown in Beil. 21, 475).

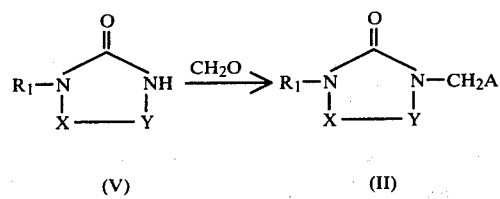

Typical examples of hydantoin N-methylols of the formula (II) (i.e. A is hydroxyl) which are used in the present invention are as shown below.

The halide of the formula (II) (i.e. A is a halogen atom such as chlorine or bromine) is readily obtained by the reaction of the alcohol of the formula (II) with a halogenating agent (e.g. phosphorus oxychloride, phosphorus trichloride, phosphorus tribromide, hydrochloric acid, hydrobromic acid, thionyl chloride) (an analogous reaction is shown in Beil. 21, 476).

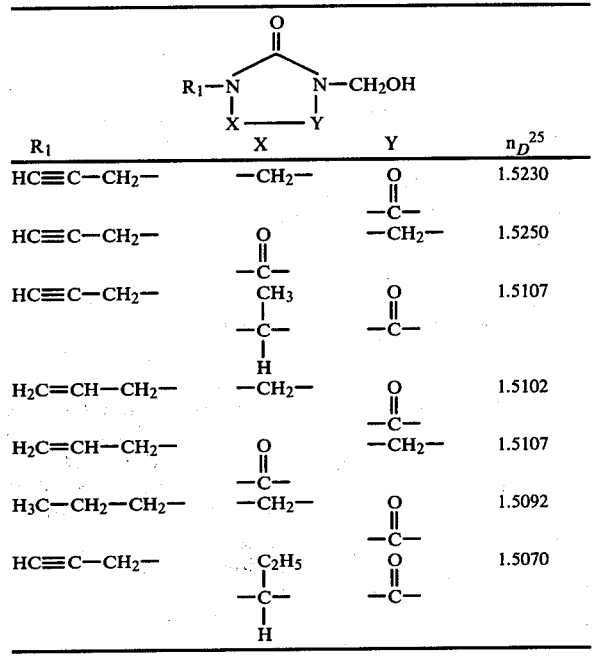

Next, examples of synthetic reaction will be explained with reference to the standard procedures.

A. Process by reaction between alcohol and carboxylic acid halide 0.05 Mole of the alcohol is dissolved in dry benzene of three times by volume, and 0.075 mole of pyridine is added thereto. Separately from this, 0.053 mole of the carboxylic acid chloride is dissolved in dry benzene of three times by volume, and the solution is added at one time to the former solution when an exothermic reaction begins. After allowing the product to stand overnight in an air-tight condition, a small amount of water is added to dissolve the precipitated pyridine hydrochloride, and the aqueous layer is separated. The organic layer is washed progressively with a 5% aqueous hydrochloric acid, aqueous solution saturated with sodium hydrogen carbonate and an aqueous solution saturated with sodium chloride, and then dried over anhydrous sodium sulfate. The benzene solution is concentrated and purified by chromatography on silica gel to obtain the objective ester.

B. Process by dehydration reaction between alcohol and carboxylic acid 0.05 Mole of the alcohol and 0.05 mole of the carboxylic acid are mixed by dissolving them in benzene of three times by volume, and 0.08 mole of dicyclohexylcarbodiimide is added thereto, followed by allowing the product to stand overnight in an air-tight condition. Next day, the reaction solution is heated under reflux for 2 hours to complete the reaction, cooled and filtered to remove the precipitated dicyclohexylurea. Thereafter, after-treatment is carried out in the same manner as in the standard procedure A to obtain the objective compound.

C. Process by reaction between alcohol and carboxylic acid anhydride 0.05 Mole of the alcohol is dissolved in toluene of three times by volume, and 0.05 mole of the carboxylic acid anhydride (synthesized from the carboxylic acid and acetic anhydride) is added thereto. The reaction solution is heated under reflux for 3 hours, and then the solution is distilled under reduced pressure or neutralized with a 5% sodium hydroxide to recover the carboxylic acid produced as a by-product. Thereafter, aftertreatment is carried out in the same manner as in the standard procedure A to obtain the objective compound.

D. Process by reaction between alcohol halide and carboxylic acid salt 0.05 Mole of the halide and 0.06 mole of the carboxylic acid are dissolved in acetone of three times by volume, and a solution of 0.08 mole of triethylamine in acetone of three times by volume is gradually added dropwise thereto at 15° to 20° C. with stirring. After addition is finished, the reaction solution is refluxed for 2 hours to complete the reaction. After cooling, the precipitated triethylamine hydrochloride is filtered off and the filtrate is freed from acetone under reduced pressure.

Three times by volume of benzene is added to the residual liquor, and aftertreatment is carried out in the same manner as in the standard procedure A to obtain the objective ester.

Typical examples of synthetic reaction according to these standard procedures will be explained hereinafter.

SYNTHETIC EXAMPLE 1

(Example according to the standard procedure A)

8.4 g of 1-propargyl-3-hydantoinylmethyl alcohol were dissolved in the mixture of 26 ml of benzene and 6 g of pyridine, and a solution of 12.0 g of dl-cis, trans-2,2-dimethyl-3-(2,2-dichlorovinyl)cylcopropanecarboxylic acid chloride in 36 ml of benzene was added dropwise thereto with stirring. After allowing the product to stand overnight, a small amount of water was added to dissolve the precipitated pyridine hydrochloride and the resulting two layers were separated from each other. The organic layer was washed progressively with a 5% aqueous hydrochloric acid, aqueous sodium hydrogen carbonate solution and aqueous solution saturated with sodium chloride, and then dried over anhydrous sodium sulfate. The benzene solution was concentrated and purified by chromatography on silica gel.

Yield was 16.7 g (93.0%)

$n_D^{19.5}$ 1.5341

|  | Elementary analysis: | | |
|---|---|---|---|
|  | C(%) | H(%) | H(%) |
| Found | 50.41 | 4.32 | 7.62 |
| Calculated | 50.15 | 4.49 | 7.80 |

SYNTHETIC EXAMPLE 2

(Example according to the standard procedure B)

8.4 g of 1-propargyl-3-hydantoinylmethyl alcohol and 9.0 g of dl-trans-2,2-dimethyl-3-(2-methylbutadienyl)cyclopropanecarboxylic acid were dissolved in 52 ml of benzene, and 16.5 g of dicyclohexylcarbodiimide was added thereto with stirring, followed by allowing the product to stand overnight. Next day, the reaction solution was heated under reflux for a further 2 hours and cooled. The precipitated dicyclohexylurea was removed by filtration and the solvent was concentrated. Thereafter, a procedure was carried out in the same manner as in Synthetic example 1.

Yield 11.1 g (67.3%)

$n_D^{20.0}$ 1.5373

|  | Elementary analysis: | | |
|---|---|---|---|
|  | C(%) | H(%) | N(%) |
| Found | 65.19 | 6.78 | 8.40 |
| Calculated | 65.43 | 6.71 | 8.48 |

SYNTHETIC EXAMPLE 3

(Process according to the standard procedure C)

8.5 g of 1-allyl-3-hydantoinylmethyl alcohol were dissolved in the mixture of 26 ml of toluene and 6 g of pyridine, and 20.4 g of α-(4-chlorophenyl)isovaleric anhydride were added thereto, followed by heating under reflux for 3 hours. After cooling, the toluene solution obtained was extracted with 5% sodium hydroxide to remove the carboxylic acid produced as a by-product, followed by washing with an aqueous solution saturated with sodium chloride. The toluene solution was then concentrated and then a procedure was carried out in the same manner as in Synthetic example 1.

Yield 13.0 g (71.0%)

$n_D^{23}$ 1.5357

|  | Elementary analysis: | | |
|---|---|---|---|
|  | C(%) | H(%) | N(%) |
| Found | 58.92 | 5.77 | 7.49 |
| Calculated | 59.26 | 5.80 | 7.68 |

SYNTHETIC EXAMPLE 4

(Process according to the standard procedure D)

9.3 g of 1-propargyl-3-hydantoinylmethyl chloride and 11.7 g of dl-trans-2,2-dimethyl-3-cyclopentylidenemethylcyclopropanecarboxylic acid were dissolved in 63 ml of acetone, and a solution of 8.1 g of triethylamine in 15 ml of acetone was added dropwise thereto. The reaction mixture was gradually heated and refluxed for 2 hours. After cooling, triethylamine hydrochloride was removed by filtration, and water and benzene were added to the filtrate which was then shaken and separated into two layers. The organic layer was progressively washed with a 5% aqueous sodium hydroxide solution and aqueous solution saturated with sodium chloride, and the solvent was then concentrated. Thereafter, a procedure was carried out in the same manner as in Synthetic example 1.

Yield 10.7 g (62.1%)

$n_D^{25.5}$ 1.5172

|  | Elementary analysis: | | |
|---|---|---|---|
|  | C(%) | H(%) | N(%) |
| Found | 66.30 | 7.08 | 8.39 |
| Calculated | 66.26 | 7.02 | 8.13 |

The carboxylic acid esters of the present invention represented by the formulae (I) and (II) are new compounds and shown by the following typical examples which are not however to be interpreted as limiting the present esters thereto.

Among the esters of the foregoing formulae (I) and (II), there are included steric isomers due to the steric configuration of the carboxylic acid and optical isomers due to the asymmetric carbon atom of the acid. But, all these isomeric esters are included in the present invention.

Compound Number

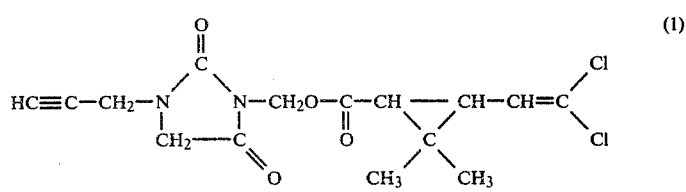

(1)

1-Propargyl-3-hydantoinylmethyl
2,2-dimethyl-3-(2,2-dichlorovinyl)cyclopropanecarboxylate (dl-Cis,trans ester: $n_D^{19.5}$ 1.5341, process A)

3-Propargyl-1-hydantoinylmethyl
2,2-dimethyl-3-(2,2-dichlorovinyl)cyclopropanecarboxylate (dl-Cis,trans ester: $n_D^{20}$ 1.5365, process A)

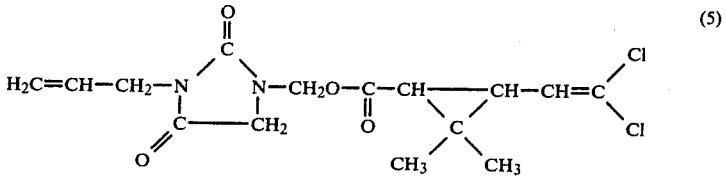
(5)

(d-Trans ester: $n_D^{22.5}$ 1.5328, process A)

3-Allyl-1-hydantoinylmethyl

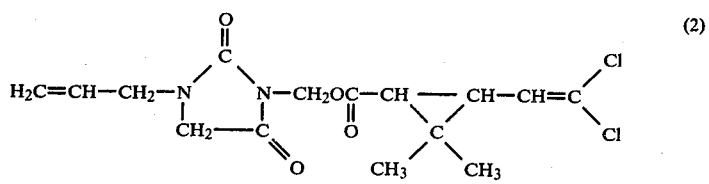
(2)

1-Allyl-3-hydantoinylmethyl
2,2-dimethyl-3-(2,2-dichlorovinyl)-cyclopropanecarboxylate (dl-Cis,trans ester: $n_D^{18}$ 1.5303, process A)

2,2-dimethyl-3-(2,2-dichlorovinyl)-cyclopropanecarboxylate (dl-Cis,trans ester: $n_D^{17.5}$ 1.5290, process A)

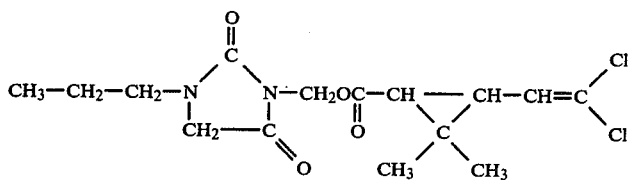
(3)

1-Propyl-3-hydantoinylmethyl
2,2-dimethyl-3-(2,2-dichlorovinyl)cyclopropanecarboxylate (dl-Cis,trans ester: $n_D^{19}$ 1.5288, process A)

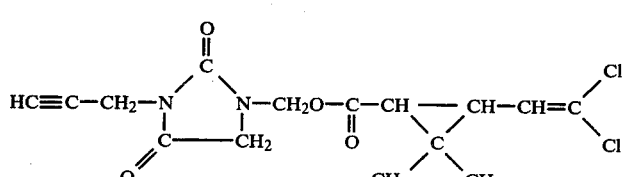
(4)

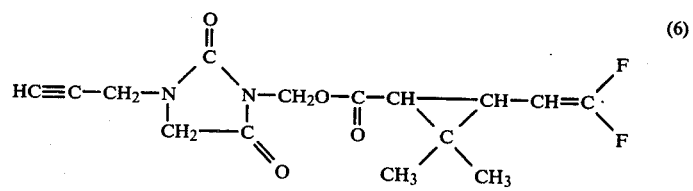
(6)

1-Propargyl-3-hydantoinylmethyl
2,2-dimethyl-3-(2,2-difluoromethyl)cyclopropanecarboxylate 1-Propargyl-3-hydantoinylmethyl
2,2,3,3-tetramethylcyclopropanecarboxylate (m.p. 86°–93° C., process C)

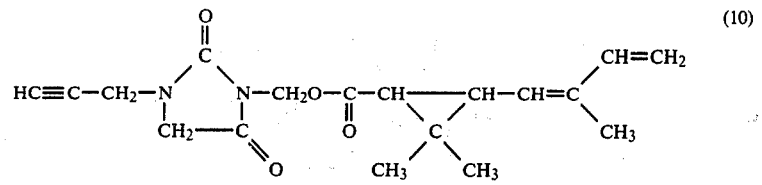
(10)

(d-Trans ester: $n_D^{20}$ 1.4925, process A)

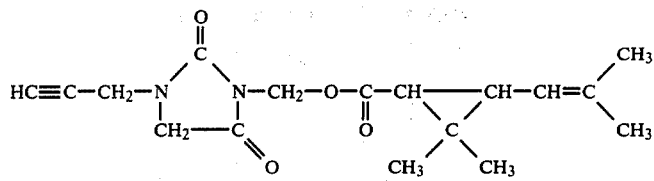
(7)

1-Propargyl-3-hydantoinylmethyl chrysanthemate
(d-Trans ester: $n_D^{19.5}$ 1.5135, process D)

1-Propargyl-3-hydantoinylmethyl
2,2-dimethyl-3-(2-methylbutadienyl)cyclopropanecarboxylate

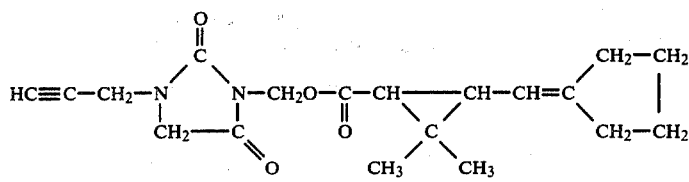
(8)

(dl-Trans ester: $n_D^{20.0}$ 1.5373, process B)

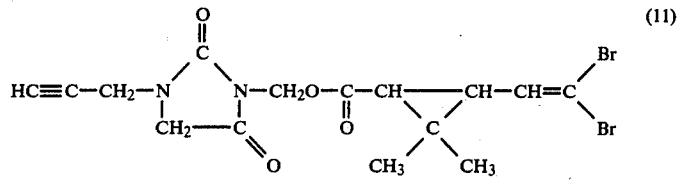
(11)

1-Propargyl-3-hydantoinylmethyl
2,2-dimethyl-3-cyclopentylidenemethylcyclopropanecarboxylate (dl-Trans ester: $n_D^{25.5}$ 1.5172, process D)

1-Propargyl-3-hydantoinylmethyl
2,2-dimethyl-3-(2,2-dibromovinyl)cyclopropanecarboxylate (d-Trans ester: $n_D^{25}$ 1.5925, process A)
(d-Cis ester: $n_D^{25}$ 1.5921, process A)

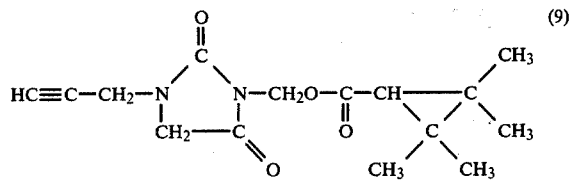
(9)

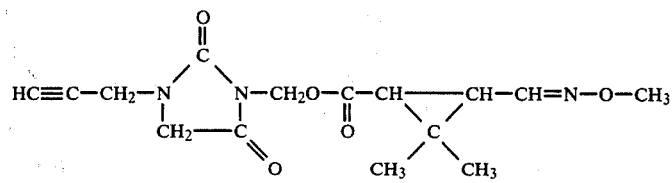
(12)

1-Propargyl-3-hydantoinylmethyl
2,2-dimethyl-3-methoxyiminomethylcyclopropanecarboxylate (d-Trans ester: $n_D^{20}$ 1.5175, process D)

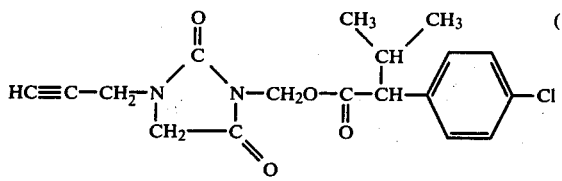
(13)

1-Propargyl-3-hydantoinylmethyl
α-(4-chlorophenyl)isovalerate ($n_D^{22.5}$ 1.5377, process C)

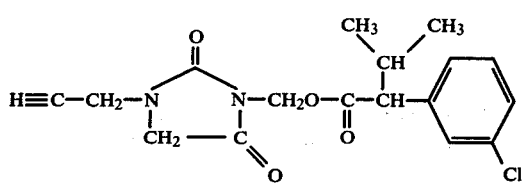
(14)

1-Propargyl-3-hydantoinylmethyl
α-(3-chlorophenyl)isovalerate ($n_D^{24}$ 1.5391, process C)

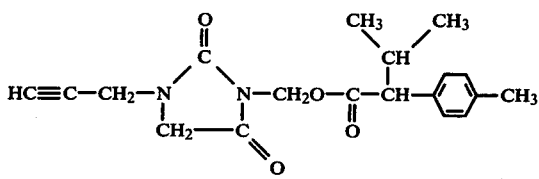
(15)

1-Propargyl-3-hydantoinylmethyl
α-(4-methylphenyl)isovalerate ($n_D^{20.0}$ 1.5257, process C)

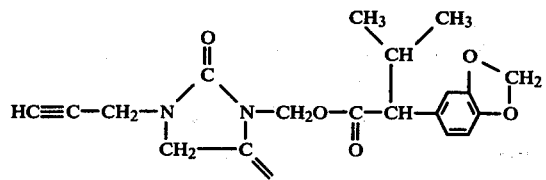
(16)

1-Propargyl-3-hydantoinylmethyl
α-(3,4-methylenedioxyphenyl)isovalerate ($n_D^{21.5}$ 1.5371, process C)

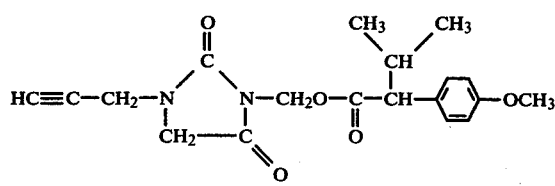
(17)

1-Propargyl-3-hydantoinylmethyl
α-(4-methoxyphenyl)isovalerate ($n_D^{22}$ 1.5290, process A)

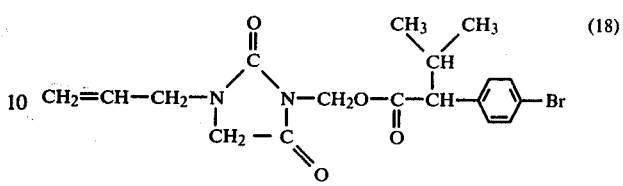
(18)

1-Allyl-3-hydantoinylmethyl
α-(4-bromophenyl)isovalerate ($n_D^{24}$ 1.5423, process A)

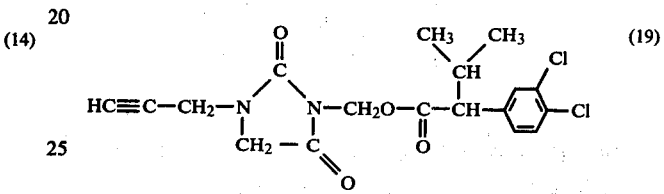
(19)

1-Propargyl-3-hydantoinylmethyl
α-(3,4-dichlorophenyl)isovalerate ($n_D^{23}$ 1.5403, process A)

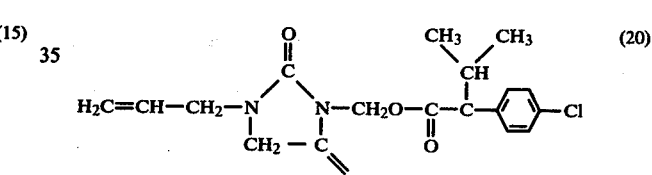
(20)

1-Allyl-3-hydantoinylmethyl
α-(4-chlorophenyl)isovalerate ($n_D^{23}$ 1.5357, process C)

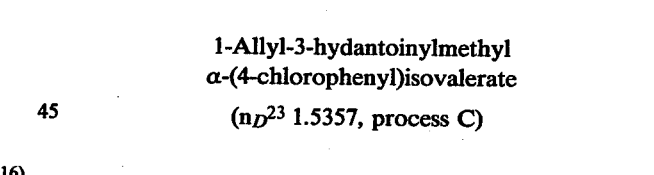
(21)

3-Propargyl-1-hydantoinylmethyl
α-(4-fluorophenyl)isovalerate ($n_D^{22}$ 1.4478, process A)

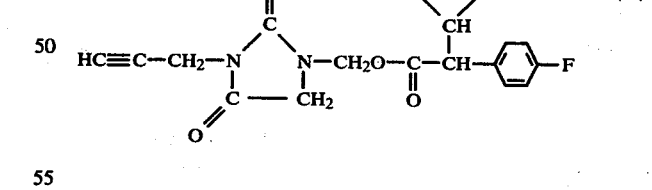
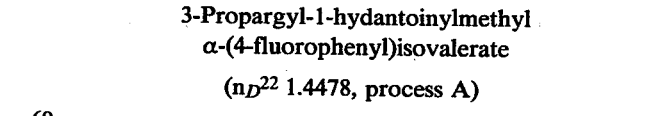
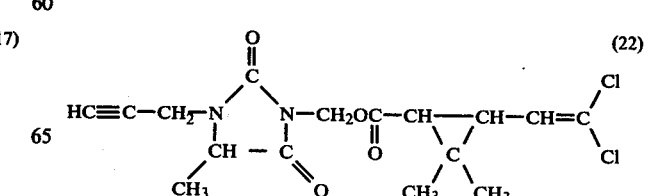
(22)

1-Propargyl-5-methyl-3-hydantoinylmethyl
2,2-dimethyl-3-(2,2-dichlorovinyl)cyclopropanecarboxylate

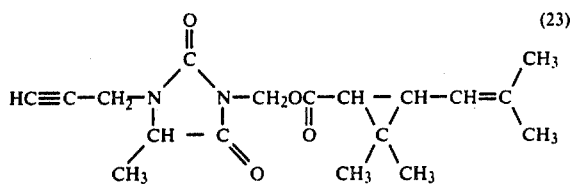
(23)

1-Propargyl-5-methyl-3-hydantoinylmethyl
chrysanthemate

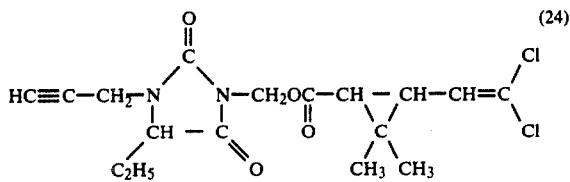
(24)

1-Propargyl-5-ethyl-3-hydantoinylmethyl
2,2-dimethyl-3-(2,2-dichlorovinyl)cyclopropanecarboxylate The compounds of the present invention represented by the formula (I) exert a very rapid effect on harmful insanitary insects and acarids such as houseflies, (*Musca domestica*), mosquitoes (Culex spp., Aedes spp. and Anopheles spp.) and cockroaches (Blattela spp. and Periplaneta spp.). Also, the compounds are very effective for controlling not only insects harmful to agricultural crops such as planthoppers (*Laodelphax striatellus, Sogatella furcifera* and *Nilaparvata lugens*), leafhoppers (Nephotettix spp.), cutworms (Spodoptera spp.) diamondback moths (*Plutella xylostella*), tortorixes (Tortricidae), aphids (Aphididae), stem-borers (Chilo spp. and Tryporyza spp.), and acarids (Tetranychus spp., Panonychus spp. and Oligonychus spp.), but also insects and acarid harmful to stored cereals such as grain mite (*Tyrophagus dimidiatus*), Indian meal moth (*Plodia interpunctella*) and rice weevil (*Sitophilus zeamais*) and animal-parasitic lyce (Anoplura) and ticks (Ixodidae). The compounds are also effective to control other harmful insects and acarids such as Onychiurus yagii, Ctenolepisma villosa, Conocephalus spp., Telegroyllus spp., *Gryllotalpa africana, Locusta migratoria*, Oxya spp., *Coptotermes formosanus, Menopon gallinae,* Damalinia spp., *Pediculus humanus,* Thripidae, *Eurydema rugosa*, Eysarcoris spp., *Halyomorpha mista, Lagymotomus elongatus,* Nezara spp., Cletus spp., Lygaeidae, Dysdercus spp., Stephanitis spp., Psyllidae, Aleyrodidae, Pseudococcidae, Coccidae, Diaspidae, Hepialidae, Tinea spp., Psychidae, Lyonetidae, Gracilariidae, Yponomeutidae, Aegeriidae, *Cnaphalocrois medinalis, Galleria mellonella,* Ostrinia spp., Heterogeneidae, Geometridae, Lasiocampidae, Lymantriidae, Notodontidae, Adris spp., Agrotis spp., Apatele spp., Heliothis spp., Leucania spp., Mamestra spp., Oraesia spp., Plusia spp., Sesamia spp., Arctiidae, Sphingidae, *Parnara guttata,* Papilio spp., Pieris spp., *Lampides boeticus,* Elateridae, Buprestidae, Dermestes spp., Lyctus spp., Anobiidae, Bostrychidae, Epilachna spp., Tenebrio spp., Cerambycidae, Chrysomelidae, Bruchidae, Curculionidae, Attelabidae, Scolytidae, Scarabaeidae, Tenthredinidae, Cynipidae, Simuliidae, Calliphoridae, Hypoderma spp., Gasterophilis spp., Trypetidae, Drosophilidae, Agromyzidae, Pulicidae and so on. Further, the compounds of the present invention not only cause the harmful insects and acarids to be knocked down and to die, but also they have repellency and flushing effect.

In formulating the present compounds of the formula (I) into insecticides and acaricides, the compounds can be formulated into optional preparation forms, like the conventional pyrethroids, using the common auxiliary diluents for insecticides and acaricides according to the methods well known to the skilled in the art, and applied to practical purposes. As the preparation forms, there may be mentioned oil sprays, emulsifiable concentrates, dusts, aerosols, wettable powders, granules, heating or non-heating fumigants such as mosquito coils, powdery or solid baits containing attractants, and the like.

By combined use of two or more of the present compounds, a stronger insecticidal and/or acaricidal activity can be developed. Further, the insecticidal and/or acaricidal effect of the present compounds can be increased in combination with the well-known synergists for pyrethroid such as α-[2-butoxyethoxy)ethoxy]-4,5-methylenedioxy-2-propyltoluene (hereinafter referred to as piperonylbutoxide), 1,2-methylenedioxy-4-[2-(octylsulfinyl)propyl]benzene (hereinafter referred to as sulfoxide), 4-(3,4-methylenedioxyphenyl)-5-methyl-1,3-dioxane (hereinafter referred to as sulfoxane), N-(2-ethylhexyl)-bicyclo[2,2,1]hepta-5-ene-2,3-dicarboximide (hereinafter referred to as MGK-264), octachlorodipropyl ether (hereinafter referred to as S-421), and isobornylthiocyano acetate (hereinafter referred to as Thanite), or with the well-known synergists for allethrin or pyrethrin.

In general, the carboxylic acid esters tend to be inferior in resistances to light, heat and oxidation. Accordingly, compositions having a more stable effect can be obtained by adding a proper amount of stabilizing agents, for example, antioxidants or UV absorbers such as phenol derivatives (e.g. 2,6-di-tert-butyl-4-methyl phenol), bisphenol derivatives, arylamines (e.g. phenyl-α-naphthylamine, phenyl-β-naphthylamine, condensation products of phenetidine and acetone) and benzophenone compounds, if necessary.

Additionally, the present compounds can be formulated into multipurpose compositions having a superior activity in combination with other active ingredients such as allethrin, N-(chrysanthemoxymethyl)-3,4,5,6-tetrahydrophthalimide (hereinafter referred to as tetramethrin), 5-benzyl-3-furylmethyl chrysanthemate (hereinafter referred to as Resmethrin), 3-phenoxybenzyl chrysanthemate (hereinafter referred to as phenothrin), 5-propargylfurfuryl chrysanthemate and 2-methyl-5-propargyl-3-furylmethyl chrysanthemate; d-trans- or d-cis,transchrysanthemic acid esters thereof; pyrethrum extracts; d-trans- or d-cis,trans-chrysanthemic acid esters of d-allethrolone; 3-phenoxybenzyl 2,2-dimethyl-3-(2,2-dichlorovinyl)-cyclopropanecarboxylate, α-cyano-3-phenoxybenzyl 2',2'-dimethyl-3'-(2,2-dichlorovinyl)-cyclopropanecarboxylate, α-cyano-3-phenoxybenzyl 2',2',3',3'-tetramethylcyclopropanecarboxylate, α-cyano-3-phenoxybenzyl 2-(4-chlorophenyl)isovalerate and other well-known cyclopropanecarboxylic acid esters; organophosphorus type insecticides, for example, O,O-dimethyl-O-(3-methyl-4-nitrophenyl)phosphorothioate (hereinafter referred to as Fenitrothion), O,O-dimethyl-O-4-cyanophenylphosphorothioate (hereinafter referred to as cyanophos), O,O-dimethyl-O-(2,2-dichlorovinyl)phosphate, Fenthion, Phenthoate, Malathion, Salithion, Dipterex and diazinon; carbamate type insecticides, for example, 1-naphthyl-N-methylcarbamate, 3,4-dimethylphenyl-N-methylcarbamate, 3-methylphenyl-N-methylcarbamate, 2-isopropoxyphenyl-N-methylcarbamate and S-methyl-N-(methylcarbamoyloxy)thioacetoimidate; N'-(2-methyl-4-chlorophenyl)-N,N-dimethylformamidine (hereinafter referred to as chlorodimeform); 1,3-bis(carbamoylthio)-2-(N,N-dimethylamino)propane hydrochloride; other insecticides, fungicides, nematocides, acaricides, plant growth regulators, microbial insecticides, insect hormone analogues, herbicides, fertilizers or other agricultural chemicals. Further, a synergistic effect due to the combination can also be expected.

Next, preparation of the present insecticides and acaricides will be illustrated with reference to the following preparation examples.

The insecticidal and/or acaricidal compositions according to this invention contain 0.001 to 80.0%, preferably 0.01 to 50% by weight of an active ingredient.

PREPARATION EXAMPLE 1

0.2 Part of each of the present compounds (1) to (24) is dissolved in kerosene and made up to 100 parts with kerosene. Thus, the oil spray of each compound is obtained.

PREPARATION EXAMPLE 2

0.05 Part of the present compound (7) and 0.25 part of piperonylbutoxide are mixed, dissolved in kerosene and made up to 100 parts with kerosene. Thus, the oil spray of the compound is obtained.

PREPARATION EXAMPLE 3

To 20 parts of each of the present compounds (1) to (24) are added 15 parts of a mixture of nonionic surfactant and anionic surfactant and 65 parts of xylene, and the mixture is well stirred to make a solution. Thus, the emulsifiable concentrate of each compound is obtained.

PREPARATION EXAMPLE 4

To 10 parts of each of the present compounds (2), (4), (7), (8), (9), (12), (13), (16) and (20) are added 20 parts of S-421, 15 parts of a mixture of nonionic surfactant and anionic surfactant and 55 parts of xylene. The mixture is well stirred to make a solution. Thus, the emulsifiable concentrate of each compound is obtained.

PREPARATION EXAMPLE 5

0.1 Part of the present compound (13), 0.2 part of tetramethrin, 7 parts of xylene and 7.7 parts of deodorized kerosene are well mixed to make a solution. The solution is placed in an aerosol container. After attaching a valve portion to the container, 85 parts of a propellant (liquefied petroleum gas) is charged therein under pressure through the valve. Thus, the aerosol of the compound is obtained.

PREPARATION EXAMPLE 6

0.3 Part of the present compound (9), 0.1 part of 3-phenoxybenzyl d-cis,trans-chrysanthemate, 7 parts of xylene and 7.6 parts of deodorized kerosene are well mixed to make a solution. Also, 0.3 part of d-trans acid isomer of the present compound (6), 0.1 part of tetramethrin, 7 parts of xylene and 7.6 parts of deodorized kerosene are well mixed to make a solution. Each solution is placed in an aerosol container and treated in the same manner as in Preparation example 5. Thus, the aerosol of each compound is obtained.

PREPARATION EXAMPLE 7

0.2 Part of the present compound (8), 0.1 part of the d-trans-chrysanthemic acid ester of allethrin, 7 parts of xylene and 7.7 parts of deodorized kerosene are well mixed to make a solution. Also, 0.2 part of the d-trans acid isomer of the present compound (11), 0.2 part of Resmethrin, 7 parts of xylene and 7.6 parts of deodorized kerosene are well mixed to make a solution. Each solution is placed in an aerosol container and treated in the same manner as in Preparation example 5. Thus, the aerosol of each compound is obtained.

PREPARATION EXAMPLE 8

To 0.6 g of each d-trans acid isomer of the present compounds (1) and (11) is added 0.4 g of BHT, and the mixture is dissolved in 20 ml of methanol. Each solution is uniformly mixed with 99 g of a mosquito coil carrier containing Tabu powder (the powder of *Machilus thunbergii*), Pyrethrum marc and wood powder in a ratio of 3:5:1, and then methanol is evaporated. To each residue is added 150 ml of water and the mixture is kneaded thoroughly, shaped into a mosquito coil and dried. Thus, the mosquito coil of each compound is obtained.

PREPARATION EXAMPLE 9

To 0.15 g of each of the present compounds (3), (5), (6), (9), (12) and (16) is added 0.2 g of the d-trans-chrysanthemic acid ester of allethrin, and the mixture is dissolved in 20 ml of methanol. Each solution is uniformly mixed with 99.65 g of a mosquito coil carrier (the same as above), and then methanol is evaporated. To each residue is added 150 ml of water and the mixture is well kneaded, shaped into a mosquito coil and dried. Thus, the mosquito coil of each compound is obtained.

PREPARATION EXAMPLE 10

To 0.1 g of each of the present compounds (6) and (14) are added 0.1 g of BHT and 0.1 g of piperonylbutoxide, and each mixture is dissolved in a suitable amount of chloroform. The solution is allowed to uniformly adsorb in a filter paper of 3.5 cm×1.5 cm×0.3 cm (thick).

Thus, a fibrous fumigant for heating on a hot plate is obtained. As the fibrous carrier, those having the same effect as pulp plate (e.g. filter paper), for example asbestos may be used.

PREPARATION EXAMPLE 11

To 0.02 g of the d-trans acid isomer of the present compound (1) are added 0.05 g of 5-propargylfurfuryl di-cis,trans-chrysanthemate and 0.1 g of BHT, and the mixture is dissolved in a suitable amount of chloroform. The solution is then allowed to uniformly adsorb in a filter paper of 3.5 cm×1.5 cm×0.3 cm (thick).

Thus, a fibrous fumigant for heating on a hot plate is obtained.

PREPARATION EXAMPLE 12

To 20 parts of each of the present compounds (3), (5), (7), (9), (12), (16), (17), (19) and (20) are added 10 parts of Fenitrothion and 5 parts of a mixture of nomionic and anionic surfactant, followed by thorough mixing. Each mixture is then well mixed with 65 parts of 300 mesh diatomaceous earth while being well stirred in a mortar. Thus, the wettable powder of each compound is obtained.

PREPARATION EXAMPLE 13

To 1 part of each of the present compounds (5), (7) and (13) is added 2 parts of 3-methylphenyl-N-methyl-carbamate, and the mixture is dissolved in 20 parts of acetone. Each solution is then well mixed with 97 parts of 300 mesh talc while being well stirred in a mortar, and then acetone is removed by evaporation. Thus, the dust of each compound is obtained.

PREPARATION EXAMPLE 14

To 3 parts of each of the present compounds (2), (8), (11), (15) and (18) are added 5 parts of lignin sulfonate derivative and 92 parts of clay, and each mixture is well mixed while being stirred in a mortar.

Then, the mixture is well mixed with water of 10% by weight based on the mixture, granulated by means of a granulator and air-dried. Thus, the granule of each compound is obtained.

PREPARATION EXAMPLE 15

To 2 parts of each of the present compounds (4), (5), (7), (13) and (20) are added 2 parts of Cyanophos, 5 parts of lignin sulfonate derivative and 91 parts of clay, and each mixture is well mixed while being stirred in a mortar.

Then, the mixture is well mixed with water of 10% by weight based on the mixture, granulated by means of a granulator and air-dried. Thus, the fine granule of each compound is obtained.

PREPARATION EXAMPLE 16

0.1 Part of the d-trans acid isomer of the present compound (1), 0.2 part of the d-trans acid isomer of allethrin, 11.7 parts of deodorized kerosene and 1 part of an emulsifying agent, namely, surfactant (glycerides of fatty acid), are well mixed and emulsified with addition of 50 parts of pure water. The emulsion is then placed in an aerosol container together with 35 parts of a 3:1 mixture of deodorized butane to deodorized propane. Thus, a water-based aerosol is obtained.

Next, preparation of the present esters and the insecticidal and acaricidal activities of the esters will be illustrated in more detail with reference to the following experimental examples.

EXPERIMENTAL EXAMPLE 1

Ten percent emulsifiable concentrates were prepared as in the Preparation example 3.

At the bottom of a polyethylene cup of 5.5 cm in diameter was placed a filter paper of the same size. 0.75 Ml of a 200-fold aqueous dilute solution of each emulsifiable concentrate (corresponding to 500 ppm) was dropped on the filter paper, and 30 mg of sucrose as a food was uniformly placed. Ten housefly female adults (*Musca domestica*) were liberated in the cup which was then covered with a lid. After 48 hours, the dead and alive were examined to obtain mortality (4 replications).

| Test compound | | Mortality (%) |
|---|---|---|
| Present compound (dl-cis,trans isomer) | (1) | 100 |
| Present compound (d-trans isomer) | (1) | 100 |
| " | (2) | 100 |
| " | (4) | 100 |
| " | (5) | 100 |
| " | (6) | 100 |
| " | (7) | 100 |
| " | (8) | 100 |
| " | (9) | 100 |
| " | (10) | 95 |
| " | (11) | 100 |
| (d-trans isomer) " | (11) | 100 |
| (d-cis isomer) " | (13) | 100 |
| " | (14) | 100 |
| " | (15) | 90 |
| " | (16) | 90 |
| " | (17) | 95 |
| " | (18) | 100 |
| " | (21) | 90 |

EXPERIMENTAL EXAMPLE 2

0.1 Part of each of the present compounds was dissolved in kerosene and made up to 100 parts with kerosene. Thus, the oil spray of each compound was obtained. Ten northern house mosquito female adults (*Culex pipiens pallens*) and 10 housefly adults (*Musca domestica*) were liberated in a (70 cm)$^3$ glass chamber. 0.7 ml of the oil spray was applied and the number of knocked down insects was counted with the lapse of time. The value of $KT_{50}$ was obtained from the mean knock-down ratio of three replications according to Finney's graphic method. After 10 minutes, the knocked down insects were collected and transferred to a recovery container and fed with a 5% sugar solution. After 24 hours, the dead and alive were examined.

| Test compound | Northern house mosquito female adult | | Housefly adult | |
|---|---|---|---|---|
| | $KT_{50}$ (sec) | Mortality (%) | $KT_{50}$ (sec) | Mortality (%) |
| Present compound (1) (dl-cis, trans acid ester) | 69" | 90 | 96" | 60 |
| Present compound (1) (d-trans acid ester) | 30" | 100 | 60" | 80 |
| Present compound (6) | 19" | 100 | 46" | 70 |
| Present compound (8) | 75" | 95 | 150" | 25 |
| Present compound (9) | 35" | 95 | 150" | 20 |
| Present compound (17) | 140" | 75 | 280" | 35 |
| Present compound (4) | 50" | 85 | 280" | 30 |
| Present compound (7) | 30" | 100 | 72" | 10 |
| Present compound (11) (d-trans acid ester) | 35" | 85 | 78" | 30 |
| Present compound (11) (d-cis acid ester) | 38" | 95 | 96" | 10 |
| Present compound (22) | 75" | 85 | 114" | 20 |
| Tetramethrin | 162" | 45 | 372" | 20 |
| Pyrethrins | 320" | 50 | >600" | 0 |

EXPERIMENTAL EXAMPLE 3

Ten northern house mosquito female adults (*Culex pipiens pallens*) were liberated in a (70 cm)$^3$ glass chamber. 0.7 Ml of each of oil sprays formulated by Preparation example 1 was sprayed and the number of knocked down mosquitoes was counted at 10 minutes after spraying.

| Test compound | KD% |
|---|---|
| (2) | 100 |
| (3) | 100 |
| (5) | 100 |
| (10) | 90 |
| (12) | 100 |
| (13) | 90 |
| (14) | 85 |
| (15) | 90 |
| (16) | 100 |
| (18) | 90 |
| (19) | 85 |
| (20) | 85 |
| (21) | 90 |
| (23) | 100 |
| (24) | 85 |
| Pyrethrins | 80 |
| Resmethrin | 50 |

EXPERIMENTAL EXAMPLE 4

Five milliliters of each of the oil sprays formulated by Preparation examples 2 was sprayed according to the Campbel's turn table method [Soap and Sanitary Chemicals, Vol. 14, No. 6, 119 (1938)] using about 100 housefly adults (*Musca domestica*) per group. The housefly adults were exposed to the descending mist for 10 minutes. The number of knocked down insects was counted at 10 minutes after spraying and a mortality count was made after 24 hours.

| Test compound | KD(%) at 10 minutes | Mortality (%) |
|---|---|---|
| (7) + piperonylbutoxicide | 100 | 95 |

EXPERIMENTAL EXAMPLE 5

Each of the emulsifiable concentrates formulated according to Preparation example 3 was diluted 100,000 times with water. Two hundred milliliters of each test solution so prepared were placed in a 300-ml glass beaker and 30 full grown larvae of northern house mosquito (*Culex pipiens pallens*) were liberated therein. By the next day, more than 90% of the larvae were killed in each case.

EXPERIMENTAL EXAMPLE 6

The insecticidal activity on housefly adults (*Musca domestica*) of each aerosol formulated according to Preparation examples 5, 6, 7 and 16 was tested by the aerosol test method (Soap and Chemical Specialities, Blue Book, 1965) using a (6 ft)$^3$ Peet Grady's chamber. Thus, with any aerosol, more than 80% of the flies could be knocked down 15 minutes after spraying and more than 70% of the flies could be killed by the next day.

EXPERIMENTAL EXAMPLE 7

About 50 northern house mosquito female adults (*Culex pipiens pallens*) were liberated in a (70 cm)$^3$ glass chamber in which a battery-type small electric fan (having a wing diameter of 13 cm) was placed and driven.

0.1 g of each of the mosquito coils formulated according to Preparation examples 8 and 9 was ignited at one end and placed at the center of the bottom of the chamber. With any mosquito coil, more than 90% of the adults could be knocked down within 20 minutes and more than 80% of the adults could be killed by the next day.

EXPERIMENTAL EXAMPLE 8

Ten adult German cockroaches (*Blattella germanica*) were liberated in a plywood-made trigonal prism like shelter with diet and water. The shelter containing cockroaches was made stand opening upward in a glass chamber (70 cm)$^3$, and 0.7 ml of 0.1% oil spray of each compound was applied to the chamber. The number of flushed out insects was counted with the lapse of time.

| Test compound | Flushing out (%) | | | | |
|---|---|---|---|---|---|
| | 38" | 75" | 150" | 300" | 600" |
| (1) (dl-cis, trans acid ester) | 35 | 65 | 75 | 85 | 95 |
| (3) | 30 | 45 | 45 | 50 | 65 |
| (6) | 47 | 74 | 79 | 79 | 100 |
| (9) | 15 | 55 | 60 | 70 | 80 |
| Pyrethrins | 15 | 20 | 35 | 40 | 50 |
| Propoxur | 0 | 0 | 0 | 0 | 5 |
| Untreated | 0 | 0 | 0 | 0 | 0 |

EXPERIMENTAL EXAMPLE 9

About 50 housefly adults (*Musca domestica*) were liberated in a (70 cm)$^3$ glass chamber in which a battery-type small electric fan (having a wing diameter of 13 cm) was placed and driven.

Each of the fumigants formulated according to Preparation examples 10 and 11 was placed on a hot plate in the chamber and fumigated. More than 90% of the houseflies could be knocked down within 20 minutes with any fumigant.

EXPERIMENTAL EXAMPLE 10

About 20 rice seedlings were grown up to a 3 to 4-leaf stage in a flower pot of 10 cm in diameter, and each of the dusts formulated according to Preparation example 13 was dusted at a rate of 3 kg/10 are by means of a Bell jar duster. After dusting, each pot was covered with a wire net, and 20 to 30 green rice leafhopper adults (*Nephotettix cincticeps*) were liberated therein. The dead and alive after 24 hours were observed, and mortality of more than 80% was obtained in each case.

EXPERIMENTAL EXAMPLE 11

Ten liters of water were placed in a 14-liter polypropylene bucket, and 1 g of each of the granular preparations formulated according to Preparation example 14 was added thereto. After one day, about 100 full grown northern house mosquito larvae (*Culex pipiens pallens*) were liberated in the water. The dead and alive were observed, and more than 90% of the larvae could be killed within 24 hours in each case.

EXPERIMENTAL EXAMPLE 12

Carmine mite female adults (*Tetranychus cinnabarinus*) were made parasitic on leaves of the potted kidney bean (primordial leaf stage) which had elapsed 9 days after sowing, at a rate of 10–15/leaf, and bred at 27° C. for a week in a constant temperature room. Then, numerous carmine mites were found to be bred at various growth stages. At this time, a 200-fold aqueous dilute solution of each of the emulsifiable concentrates formulated from the present compounds (2), (6), (8), (9) and (13) according to Preparation example 3 was sprayed at a rate of 10 ml/pot by means of a turn table. After 10 days, damage of kidney bean by the mites was examined, but hardly any damage was observed in each case.

What is claimed is:

1. A compound represented by the formula,

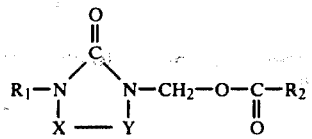

wherein one of X and Y is a carbonyl group and the other is a methylene, ethylidene or propylidene group, $R_1$ is a lower alkyl, lower alkenyl or lower alkynyl having up to 3 carbon atoms, $R_2$ is a group represented by the formula,

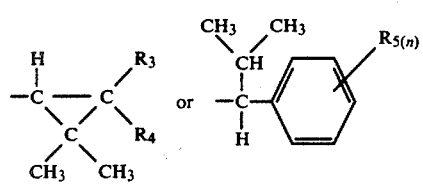

in which $R_3$ is a hydrogen atom or a methyl group; when $R_3$ is a hydrogen atom, $R_4$ is a methoxyiminomethyl or 2,2-disubstituted vinyl group in which substituents can be selected from the group consisting of methyl, vinyl, fluorine, chlorine and bromine, or both of substituents may form a tetramethylene chain; when $R_3$ is a methyl group, $R_4$ is a methyl group; $R_5$ is a methyl, methoxy, fluorine, chlorine, bromine or 3,4-methylenedioxy group; and n is 1 or 2.

2. A compound according to claim 1 represented by the formula,

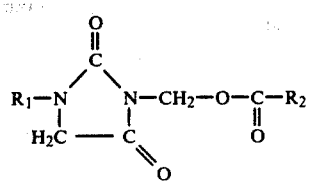

wherein $R_1$ and $R_2$ are as defined in claim 1.

3. The compound according to claim 1 represented by the formula,

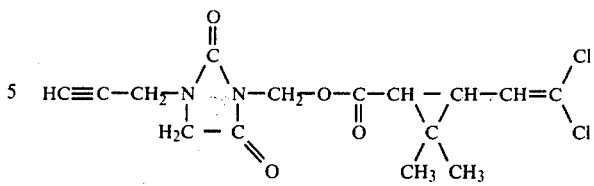

4. The compound according to claim 1 represented by the formula,

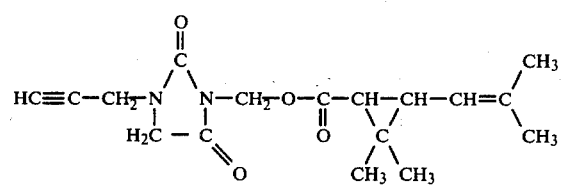

5. The compound according to claim 1 represented by the formula,

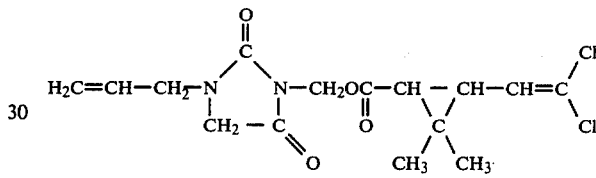

6. The compound according to claim 1 represented by the formula,

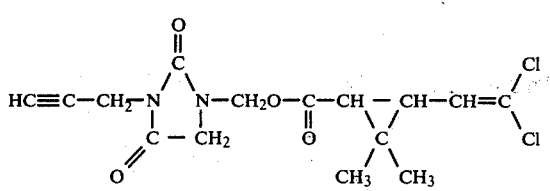

7. The compound according to claim 1 represented by the formula,

8. The compound according to claim 1 represented by the formula,

9. The compound according to claim 1 represented by the formula,

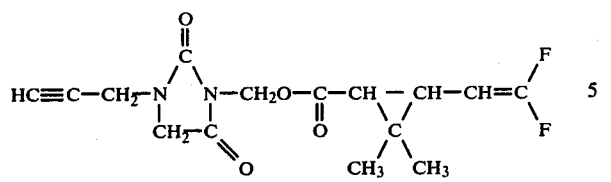

10. The compound according to claim 1 represented by the formula,

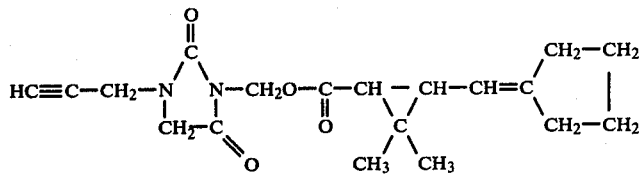

11. The compound according to claim 1 represented by the formula,

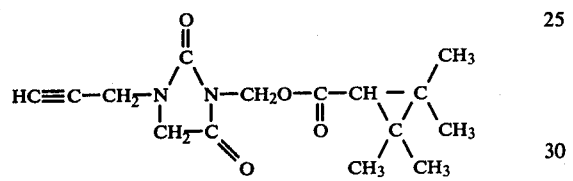

12. The compound according to claim 1 represented by the formula,

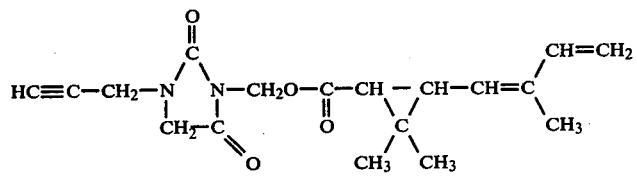

13. The compound according to claim 1 represented by the formula,

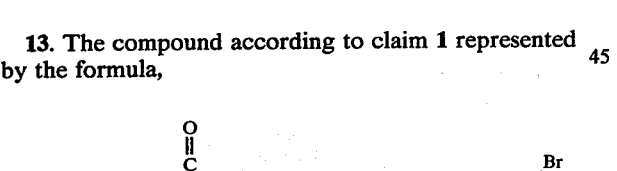

14. The compound according to claim 1 represented by the formula,

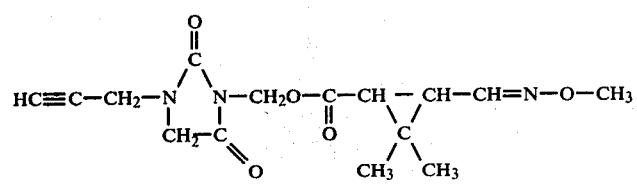

15. The compound according to claim 1 represented by the formula,

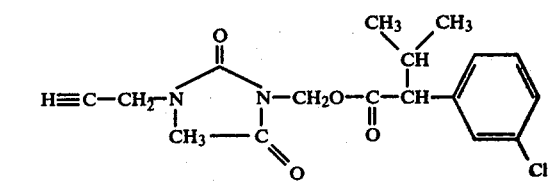

16. The compound according to claim 1 represented by the formula,

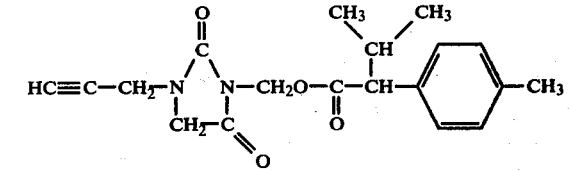

17. The compound according to claim 1 represented by the formula,

18. The compound according to claim 1 represented by the formula,

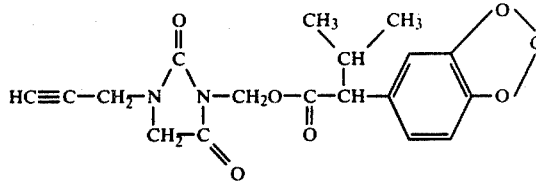

19. The compound according to claim 1 represented by the formula,

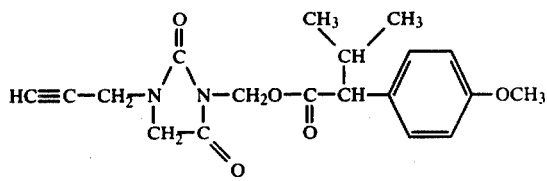

20. The compound according to claim 1 represented by the formula,

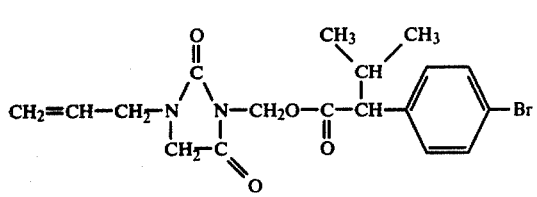

21. The compound according to claim 1 represented by the formula,

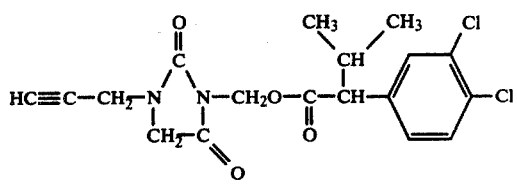

22. The compound according to claim 1 represented by the formula,

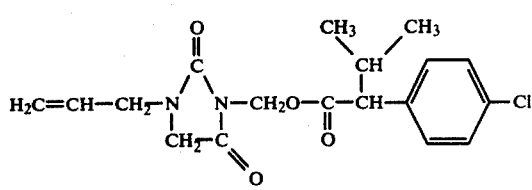

23. The compound according to claim 1 represented by the formula,

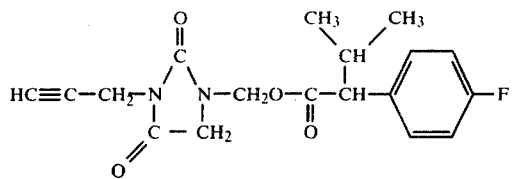

24. The compound according to claim 1 represented by the formula,

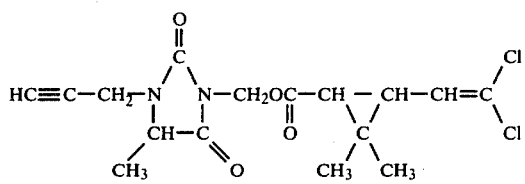

25. The compound according to claim 1 represented by the formula,

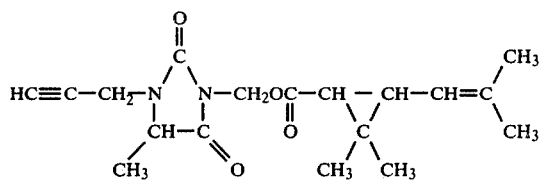

26. The compound according to claim 1 represented by the formula,

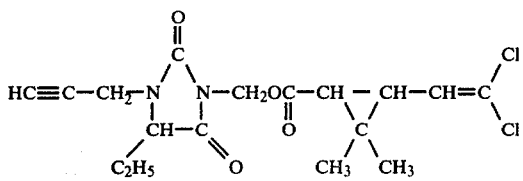

27. An insecticidal and acaricidal composition comprising an inert carrier and as the active ingredient an insecticidally and acaricidally effective amount of a compound according to claim 1.

28. The insecticidal and acaricidal composition according to claim 27, wherein the composition is in the form of an oil spray, emulsifiable concentrate, dust, aerosol, wettable powder, granule, fine granule, mosquito coil, heating or non-heating fumigant, bait or thermal fogging agent.

29. A process for controlling an insect and acarid, which comprises contacting the insect and acarid with an insecticidally and acaricidally effective amount of a compound according to claim 1.

* * * * *